United States Patent [19]
Kagotani et al.

[11] Patent Number: 5,653,853
[45] Date of Patent: Aug. 5, 1997

[54] METHOD OF REMOVING IODINE COMPOUNDS FROM CRUDE ACETIC ANHYDRIDE

[75] Inventors: Masahiro Kagotani, Hyogo; Yasuo Tsuji, Hiroshima, both of Japan

[73] Assignee: Daicel Chemical Industries, Ltd., Osaka, Japan

[21] Appl. No.: 657,427

[22] Filed: Jun. 3, 1996

Related U.S. Application Data

[63] Continuation of Ser. No. 248,732, May 25, 1994, abandoned.

[30] Foreign Application Priority Data

May 31, 1993 [JP] Japan ............... 5-128631

[51] Int. Cl.$^6$ ............... B01D 3/06; B01D 3/34; C07C 51/44
[52] U.S. Cl. ............... 203/33; 203/38; 203/73; 203/74; 203/88; 203/99; 203/DIG. 19; 562/608
[58] Field of Search ............... 203/88, 38, 33, 203/73, 74, 99, DIG. 6, DIG. 19, 29; 562/608; 560/248

[56] References Cited

U.S. PATENT DOCUMENTS

| | | |
|---|---|---|
| 3,425,798 | 2/1969 | Statman et al. . |
| 4,340,569 | 7/1982 | Davidson et al. . |
| 4,399,001 | 8/1983 | Hartmann et al. ............ 203/70 |
| 4,664,753 | 5/1987 | Erpenbock et al. ............ 203/38 |
| 4,994,608 | 2/1991 | Torrena et al. ............ 203/88 |
| 5,026,908 | 6/1991 | Smith et al. ............ 203/88 |
| 5,175,362 | 12/1992 | Fillers et al. ............ 562/608 |
| 5,227,520 | 7/1993 | Cooper ............ 203/88 |
| 5,387,713 | 2/1995 | Cook et al. ............ 562/608 |
| 5,466,876 | 11/1995 | Harron et al. ............ 562/608 |
| 5,502,249 | 3/1996 | Fillers et al. ............ 203/DIG. 6 |

FOREIGN PATENT DOCUMENTS

| | | |
|---|---|---|
| 0075730 | 4/1983 | European Pat. Off. . |
| 0132391 | 1/1985 | European Pat. Off. . |
| 58-116436 | 7/1983 | Japan . |
| 61-8811 | 3/1986 | Japan . |

*Primary Examiner*—Virgina Manoharan
*Attorney, Agent, or Firm*—Flynn Thiel, Boutell & Tanis, P.C.

[57] ABSTRACT

A process by which iodine compounds contained in crude acetic anhydride or a mixture of crude acetic anhydride and crude acetic acid can be converted into methyl iodide having a low boiling point and which can be separated by distillation and efficiently removed by the combination of the conversion step with the heat treatment step and distillation step. The process includes the steps of heat-treating the crude acetic anhydride or the mixture of crude acetic anhydride and crude acetic acid in the presence of methanol and/or methyl acetate in a treatment tank and distilling the heat-treated crude acetic anhydride or the heat-treated mixture of crude acetic anhydride and crude acetic acid, in the presence of an alkali metal salt and/or an alkaline earth metal salt if necessary.

6 Claims, No Drawings

METHOD OF REMOVING IODINE COMPOUNDS FROM CRUDE ACETIC ANHYDRIDE

This application is a continuation of U.S. Ser. No. 08/248,732, filed May 25, 1994, now abandoned.

BACKGROUND OF THE INVENTION

1. Field of the Invention

The present invention relates to a method of removing iodine compounds from crude acetic anhydride or a mixture of crude acetic anhydride and crude acetic acid, i.e., a carbonylation reaction product.

2. Description of the Related Art

Acetic anhydride is used on a large scale as a starting material for cellulose acetate, and it is useful also as a starting material for chemicals such as medicines, perfumes and dyes. Acetic acid, which is also used on a large scale as a starting material for acetic esters, acetic anhydride, vinyl acetate and terephthalic acid, is a fundamental compound required in the polymer industry, the chemical industry and many other industries.

Acetic anhydride was produced from a ketene obtained by thermal decomposition of acetic acid in the prior art. Recently a process for producing acetic anhydride from methyl acetate or dimethyl ether, and carbon monoxide has been developed. This process comprises conducting a catalytic reaction in the presence of a rhodium compound and methyl iodide as the main catalysts. Various cocatalysts have been proposed, however, since the reaction velocity is low when only the main catalysts are used. The function required of The cocatalyst is to accelerate the reaction of methyl acetate or dimethyl ether with carbon monoxide to an industrially acceptable extent. It is also required of the cocatalyst to exhibit a remarkable acceleration effect in as small as possible amount. When no cocatalyst is used, the reaction velocity does not depend on the concentration of the rhodium compound and methyl iodide used as the main catalysts but it heavily depends on the concentration of methyl acetate. Thus, the productivity of the reaction is very poor. On the other hand, when the cocatalyst is used, the dependence of the reaction velocity on the concentration of methyl acetate is reduced and the reaction velocity comes to depend on the concentration of the rhodium compound and methyl iodide used as the main catalysts.

As the reaction promoters, various cocatalysts are proposed such as iodides of quaternized amine compounds and phosphine compounds, lithium compounds such as lithium iodide and lithium acetate and Lewis acid compounds such as aluminum compounds and chromium compounds. Among these cocatalysts, the iodides of quaternized amine compounds and phosphine compounds have a relatively poor reaction-promoting effect and, therefore, they must be used in a large amount. Lithium compounds such as lithium iodide and lithium acetate must be used also in an amount of as large as 30 to 50 mol or above per mole of rhodium. Although Lewis acid compounds such as aluminum compounds, chromium compounds and zirconium compounds exhibit their excellent effect in an amount of as small as about 10 mol per mole of rhodium, it is necessary that an alkali metal iodide or the like is further added to the reaction system in order to stabilize rhodium and the cocatalyst per se.

Although the reactivity is improved by using a large amount of such a cocatalyst containing iodide ions or a Lewis acid compound together with an alkali metal iodide, the iodide ion concentration in the reaction liquid is increased to increase the concentration of ionizable iodine compounds (i.e. an iodine compound which releases iodide ions upon reaction with water), i.e. the concentration of iodine compounds such as acetyl iodide, hydrogen iodide and inorganic iodine salts in the reaction liquid. When the concentration of such ionizable iodine compounds in the reaction liquid is high, the amount of iodine compounds, other than methyl iodide used as the cocatalyst, such as acetyl iodide and hydrogen iodide as contaminants is increased in the reaction mixture comprising the intended acetic anhydride obtained in the form of vapor. As a result, much labor is required for removing iodine contaminant from crude acetic anhydride or from a mixture of crude acetic anhydride and crude acetic acid and, in addition, another problem of corrosion of the apparatus is caused in the step of purifying the product.

Various processes have hitherto been proposed for removing iodine compounds from a carbonylation reaction product. For example, a process wherein crude carboxylic acid is distilled in the presence of an alcohol to obtain highly purified carboxylic acid; and a process wherein a methanol stream is introduced into a lower part of a distillation column to obtain acetic acid substantially free from hydrogen iodide and methyl iodide [see U.S. Pat. No. 4,039,395 (patented on Aug. 2, 1977; assignee: MONSANTO CO.)] have been proposed. As the result of the investigations made by the present inventors, it was found that although the iodine concentration was lowered to a practical level after the treatment when the liquid to be treated had a low iodine concentration, the complete removal of iodine from the liquid to be treated in the distillation column was difficult when the liquid to be treated had a high iodine concentration in these processes.

A process, wherein a carbonylation product is treated with peracetic acid and diacetyl peroxide and then the product is separated by distillation to reduce the total amount of iodine in the liquid after treatment to 20 ppb or below, has been disclosed. However, also in this process, the total iodine amount in the carbonylation product to be treated is limited to 100 ppm or below, and in addition, the handling of remaining unreacted peracetic acid and diacetyl peroxide is troublesome, since they might cause an explosion by violent reaction thereof. Thus, in practice, this technique cannot be easily applied to the plant unfavorably.

Japanese Patent Publication-A No. 58-118438 (published on Jul. 11, 1983) proposes a process wherein an alkali metal and/or an alkali metal oxide, hydroxide, carbonate or hydrogencarbonate is introduced into acetic anhydride in the distillation step. Although this process is effective in removing iodides having a concentration of not above 100 ppm, a large amount of the alkali metal and/or the alkali metal oxide, hydroxide, carbonate or hydrogencarbonate is necessitated when the iodide concentration in the liquid to be treated is high.

Japanese Patent Publication-B No. 61-8811 (published on Mar. 18, 1986) discloses a process for purifying crude acetic acid by adding methyl acetate to the crude acetic acid containing 1 to 5,000 ppm (determined as the amount of iodine) of iodine compounds in the distillation column before distillation. Although the iodine concentration in the resulting acetic acid is reduced to 0.1 ppm by the purification when the concentration of the iodine compounds in the crude acetic acid to be treated is as low as 20 ppm as described in the Examples of the above patent document, this process also has a defect that the iodine concentration cannot be reduced to 1 ppm or below when the concentration of the iodine compounds in the crude acetic acid to be treated is high.

To remove iodine compounds from crude acetic anhydride or a mixture of crude acetic anhydride and crude acetic acid, the process described in the above U.S. Pat. No. 4,039,395 wherein methanol is introduced into a distillation column and the process described in the above Japanese Patent Publication-B No. 61-8811 wherein methyl acetate is introduced into a distillation column may be employed. Although these processes are effective in the case of acetic acid alone, it has been found that these processes have the following defects in addition to the above-described defects when also acetic anhydride is contained: i.e., methanol rapidly reacts with acetic anhydride to form methyl acetate, which has such a low reactivity with hydrogen iodide and acetyl iodide in crude acetic anhydride that no sufficient reaction of the methyl acetate with hydrogen iodide and acetyl iodide can be effected by their mere contact during distillation in the distillation column and, therefore, no intended effect can be obtained unless an impractically large amount of methyl acetate is introduced into the distillation column.

Therefore, an object of the present invention is to provide an effective method of removing ionic iodine compounds such as acetyl iodide and hydrogen iodide from crude acetic anhydride or a mixture of crude acetic anhydride with crude acetic acid formed by continuously reacting dimethyl ether and/or methyl acetate, and optionally water and/or methanol, with carbon monoxide alone or both carbon monoxide and hydrogen, in the presence of a rhodium compound as a catalyst, methyl iodide as a cocatalyst and an iodide as a reaction promoter.

DISCLOSURE OF THE INVENTION

SUMMARY OF THE INVENTION

After extensive investigations made for the purpose of attaining the above-described object, the present inventors have found a method of effectively removing iodine compounds, such as hydrogen iodide and acetyl iodide, which are difficult to separate by mere distillation from the crude acetic anhydride or the mixture of crude acetic anhydride and crude acetic acid formed by reacting dimethyl ether and/or methyl acetate, and optionally water and/or methanol, with carbon monoxide alone or both carbon monoxide and hydrogen, in the presence of a rhodium compound as a catalyst and methyl iodide as a cocatalyst. The present invention has been accomplished on the basis of this finding.

Thus, the present invention provides a method of removing iodine compounds contained in crude acetic anhydride or a mixture of crude acetic anhydride and crude acetic acid formed by reacting dimethyl ether and/or methyl acetate, and optionally water and/or methanol, with carbon monoxide in the presence or absence of hydrogen in the presence of a rhodium compound as a catalyst and methyl iodide as a cocatalyst, which comprises the steps of heat-treating the crude acetic anhydride or the mixture of crude acetic anhydride and crude acetic acid in the presence of methanol and/or methyl acetate in a treatment tank and distilling the heat-treated crude acetic anhydride or the heat-treated mixture of crude acetic anhydride and crude acetic acid.

The crude acetic anhydride or the mixture of crude acetic anhydride and crude acetic acid is preferably formed by reacting dimethyl ether, methyl acetate, a dimethyl ether/methanol mixture or a methyl acetate/methanol mixture, with carbon monoxide alone or both carbon monoxide and hydrogen.

The crude acetic anhydride or the mixture of crude acetic anhydride and crude acetic acid is generally formed in the presence of an iodide as a reaction promoter.

The heat-treatment is advantageously effected at 110° to 200° C. for 5 to 60 minutes.

Another heat-treatment in a distillation column at a residence time of at least 5 min may also be effected.

The crude acetic anhydride or the mixture of crude acetic anhydride and crude acetic acid to be heat-treated is generally obtained by taking a crude reaction liquid out of the reactor, subjecting the crude reaction liquid to flash evaporation to give a vapor comprising acetic anhydride or a vapor comprising acetic anhydride and acetic acid, introducing the vapor into a distillation column, and taking out the crude acetic anhydride or the mixture of crude acetic anhydride and crude acetic acid through a side stream near the bottom of the distillation column.

The distillation is preferably effected in the presence of an alkali metal salt and/or an alkaline earth metal salt.

The method of removing iodine compounds may further comprise the step of distilling the crude acetic anhydride or the mixture of crude acetic anhydride and crude acetic acid before the heat-treatment.

Further, the present invention provides a process for producing acetic anhydride or a mixture of acetic anhydride and acetic acid, which comprises the steps of reacting dimethyl ether and/or methyl acetate, and optionally water and/or methanol, with carbon monoxide in the presence or absence of hydrogen in the presence of a rhodium compound as a catalyst and methyl iodide as a cocatalyst to give crude acetic anhydride or a mixture of crude acetic anhydride and crude acetic acid, heat-treating the crude acetic anhydride or the mixture of crude acetic anhydride and crude acetic acid in the presence of methanol and/or methyl acetate in a treatment tank and distilling the heat-treated crude acetic anhydride or the heat-treated mixture of crude acetic anhydride and crude acetic acid.

The present invention provides a method of removing iodine compounds contained in crude acetic anhydride or a crude acetic anhydride/crude acetic acid mixture characterized in that in the process for producing acetic anhydride or an acetic anhydride/acetic acid mixture by reacting dimethyl ether, methyl acetate, a dimethyl ether/methanol mixture or a methyl acetate/methanol mixture with carbon monoxide alone or both carbon monoxide and hydrogen in the presence of a rhodium compound as a catalyst and methyl iodide as a cocatalyst, the crude acetic anhydride or the crude acetic anhydride/crude acetic acid mixture is heat-treated in the presence of methanol and/or methyl acetate in a treatment tank.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The crude acetic anhydride or the mixture of crude acetic anhydride and crude acetic acid to be heat-treated by the method of the present invention is obtained by reacting dimethyl ether and/or methyl acetate with carbon monoxide in the presence or absence of hydrogen in the presence of a rhodium compound as the main catalyst and methyl iodide as the cocatalyst. When it is intended to prepare a mixture of acetic anhydride and acetic acid, it is possible to use also methanol and/or water in the step of carbonylating dimethyl ether and/or methyl acetate.

Examples of the starting material to be reacted with carbon monoxide include dimethyl ether, methyl acetate, a dimethyl ether/methyl acetate mixture, a dimethyl ether/methanol mixture, a methyl acetate/methanol mixture, a dimethyl ether/water mixture, a methyl acetate/water mixture, a dimethyl ether/methyl acetate/methanol mixture, a dimethyl ether/methyl acetate/water mixture, a dimethyl ether/methanol/water mixture and a methyl acetate/methanol/water mixture. However, the starting material to be reacted with carbon monoxide is not limited to them, and any combination can be used as long as dimethyl ether and/or methyl acetate is(are) present.

The concentration of rhodium in the reaction liquid is 100 to 10,000 ppm, preferably 300 to 3,000 ppm. The concentration of methyl iodide in the reaction liquid is 10 to 30% by weight, that of methyl acetate is 5 to 40% by weight, that of acetic anhydride is 10 to 40% by weight and that of acetic acid is 0 to 40% by weight. The reaction is conducted in the presence of carbon monoxide alone or both carbon monoxide and hydrogen. The partial pressure of carbon monoxide is 5 to 70 atm, that of hydrogen is 0 to 10 atm, the total pressure is 6 to 130 atm and the reaction temperature is 150° to 250° C.

The reaction promoters to be added to the reaction liquid include iodides of quaternized amine compounds and phosphine compounds; lithium compounds such as lithium iodide and lithium acetate; and Lewis acidic metal compounds such as aluminum compounds and chromium compounds. The amount of the reaction promoter is 5 to 100 mol, preferably 5 to 50 mol, per mole of rhodium. The aluminum compounds exhibit their marked effect when they are used in such an amount that the amount of aluminum atom of the aluminum compound(s) is about 10 to 20 mol per mole of rhodium, and, in such a case, a boron compound may be added thereto in order to stabilize the promoter, i.e., the aluminum compound. The boron compounds usable herein include boric acid, metaboric acid, etc. The boron compounds are used in such an amount that the amount of boron atom of the boron compound(s) is 1 to 10 mol per mole of aluminum atom. An iodine compound can be added as a stabilizer for rhodium in addition to the reaction promoter. The reaction promoter can be used either singly or in combination of two or more of them.

The crude reaction liquid obtained by the reaction conducted in the presence of the catalyst, cocatalyst and reaction promoter is taken out of the reactor to subject flash evaporation, so that the crude reaction liquid is divided into an unevaporated, circulating catalyst solution containing the catalyst and a vapor comprising acetic anhydride or a vapor comprising acetic anhydride and acetic acid. The circulating catalyst solution is recycled to the reactor. The vapor is directly introduced into a distillation column. Low-boiling components such as methyl iodide and methyl acetate are taken out through the top of the column, and crude acetic anhydride containing methyl acetate or a mixture of crude acetic anhydride and crude acetic acid containing methyl acetate is obtained through a side stream near the bottom of the column. A high-boiling fraction containing a very small amount of the catalyst is taken through the bottom of the column and recycled to the reactor.

The crude acetic anhydride or the mixture of crude acetic anhydride and crude acetic acid, which contains methyl acetate and is taken out through the side stream near the bottom of the column, contains iodine compounds such as hydrogen iodide and acetyl iodide which could not be separated by only the distillation of the prior art.

In the present invention, the crude acetic anhydride or the mixture of crude acetic anhydride and crude acetic acid is heat-treated in the presence of methanol and/or methyl acetate in a treatment tank. Namely, after the crude acetic anhydride or the mixture of crude acetic anhydride and crude acetic acid is introduced into a treatment tank, methanol and/or methyl acetate is added thereto and the resultant mixture is heat-treated. Alternatively, the crude acetic anhydride or the mixture of crude acetic anhydride and crude acetic acid is introduced into a treatment tank containing therein methanol and/or methyl acetate introduced thereinto and the resultant mixture is heat-treated. Or, methanol and/or methyl acetate is added to the crude acetic anhydride or the mixture of crude acetic anhydride and crude acetic acid, the resultant mixture is introduced into a treatment tank and then heat-treated therein. When unreacted methyl acetate, which is used as a starting material, is contained in a sufficient amount in the crude acetic anhydride or the mixture of crude acetic anhydride and crude acetic acid, the addition of methyl acetate is not always necessitated.

The heat treatment is conducted either batchwise or continuously at 110° to 200° C. The treatment time is 5 to 60 min, preferably 10 to 30 min. The amount of methanol and/or methyl acetate to be present is 1 to 1,000 mol, preferably 10 to 500 mol, per mole of the iodine compound to be treated. The molar concentration of the iodine compound to be treated is determined by adding water to the crude acetic anhydride or the mixture of crude acetic anhydride and crude acetic acid to isolate iodide ions from hydrogen iodide and acetyl iodide and subjecting them to quantitative analysis.

The heat-treated crude acetic anhydride or the heat-treated crude acetic anhydride/acetic acid mixture is introduced into a distillation column and distilled therein. In the distillation column, the crude acetic anhydride or the crude acetic anhydride/acetic acid mixture can be brought into contact with methanol, methyl acetate, an alkali metal salt and/or an alkaline earth metal salt or a solution containing the alkali metal salt and/or alkaline earth metal salt to remove the iodine compounds. Particularly, the remaining iodine compounds can be effectively removed by bringing the crude acetic anhydride or the crude acetic anhydride/acetic acid mixture into contact with the solution containing the alkali metal salt and/or alkaline earth metal salt. In other words, the distillation is preferably effected in the presence of an alkali metal salt and/or an alkaline earth metal salt.

Effectively usable alkali metal salts and alkaline earth metal salts are, for example, alkali metal and alkaline earth metal hydroxides, acetates and carbonates such as KOH, $K_2CO_3$, $KHCO_3$, NaOH, $Na_2CO_3$, $NaHCO_3$, $Ca(OH)_2$, $CaCO_3$, $Ca(HCO_3)_2$, $Ba(OH)_2$, $BaCO_3$ and $Ba(HCO_3)_2$. The alkali or alkaline earth metal salt is used in such as amount that the amount of the alkali or alkaline earth metal atom is 1 to 10 mol per mole of the remaining iodine compound, and the concentration of the alkali or alkaline earth metal salt in the solution is 0.1 to 50% by weight.

The alkali metal salt and/or alkaline earth metal salt or a solution thereof may be brought into contact with the crude acetic anhydride to be distilled or the crude acetic anhydride/acetic acid mixture to be distilled before they are fed into the distillation column to feed the resultant mixture into the distillation column or, alternatively, it may be fed into the distillation column through a section above the charge port of the distillation column. Further, it may be fed in such a manner that it will be combined with the reflux liquid at the top of the distillation column. It is also possible to employ a treatment tank system wherein the alkali or alkaline earth metal salt or the solution thereof is fed into the treatment tank in place of the distillation column system.

In the present invention, the step of distilling the crude acetic anhydride or the mixture of crude acetic anhydride and crude acetic acid before the heat-treatment may be effected.

Examples of the above-described series of the treating steps to be conducted in the presence of methanol and/or methyl acetate include ② the process which comprises feeding crude acetic anhydride or a crude acetic anhydride/acetic acid mixture containing iodine compounds such as hydrogen iodide and acetyl iodide into a treatment tank, heat-treating it and introducing it into a distillation column to distill it; ② the process which is as same as the above process ①, except that the distillation is conducted in the presence of an alkali or alkaline earth metal salt or with the use of an alkali or alkaline earth metal salt solution; ③ the process which comprises feeding crude acetic anhydride or a crude acetic anhydride/acetic acid mixture containing iodine compounds such as hydrogen iodide and acetyl iodide into a distillation column, heat-treating it for a residence time of at least 5 min, and taking out purified acetic anhydride or a purified acetic anhydride/purified acetic acid mixture through a side stream; ④ the process which comprises conducting the above process ③ in the presence of an alkali or alkaline earth metal salt or with the use of an alkali or alkaline earth metal salt solution; ⑤ the process which comprises feeding crude acetic anhydride or a crude acetic anhydride/acetic acid mixture containing iodine compounds such as hydrogen iodide and acetyl iodide into a distillation column, heat-treating it therein for a residence time of at least 5 min, withdrawing the treated liquid through the bottom of the column, introducing it into a treatment tank, heat-treating it therein, and feeding into the distillation column to distill it; ⑥ the process which is the same as the above process ⑤, except that the distillation is conducted in the presence of an alkali or alkaline earth metal salt or with the use of an alkali or alkaline earth metal salt solution; ⑦ the process which is the same as the above processes ⑤ or ⑥, except that the heat treatment in the treatment tank is conducted in the presence of an alkali or alkaline earth metal salt or with the use of an alkali or alkaline earth metal salt solution; and ⑧ the process which comprises feeding crude acetic anhydride or a crude acetic anhydride/acetic acid mixture containing iodine compounds such as hydrogen iodide and acetyl iodide into a treatment tank to conduct the heat treatment, then into the next treatment tank to conduct the heat treatment in the presence of an alkali or alkaline earth metal salt or with the use of an alkali or alkaline earth metal salt solution, and then into a distillation column to conduct the distillation in the presence of an alkali or alkaline earth metal salt or with the use of an alkali or alkaline earth metal salt solution. However, the processes are not limited to the above-described ones and any combination of the steps is possible so far as it includes the heat-treatment step and the distillation step.

The process of the present invention enables the iodine compounds contained in crude acetic anhydride or a mixture of crude acetic anhydride and crude acetic acid to be converted into methyl iodide having a low boiling point and separable by distillation. Therefore, efficient removal of the iodine compounds can be attained by the combination of the conversion step with the heat treatment step and distillation step in the present invention.

EXAMPLES

The present invention will now be described in more detail with reference to the following Examples which should not be considered to limit the scope of the present invention.

Example 1

3 kg/h of acetic anhydride and 3 kg/h of acetic acid were produced in a pilot plant equipped with a 20-l reactor. The concentration of rhodium in the reaction liquid was 1,000 ppm, that of methyl iodide was 15% by weight and that of methyl acetate was 25% by weight. Aluminum acetate and lithium iodide as the reaction promoters and boric acid as the catalyst stabilizer were used in amounts of 10 mol, 20 mol and 20 mol, respectively, per mole of rhodium. The reaction temperature was 190° C. and the reaction pressure was 30 kg/cm². The reaction liquid was withdrawn from the reactor and introduced into an evaporation tank in which the pressure was regulated to 1.4 kg/cm², and flash-evaporated therein. The evaporated compounds in gaseous form were fed into the first distillation column and distilled therein, while the liquid phase containing the catalyst which had not been evaporated in the flash evaporation step was recycled to the reactor. Low-boiling-point by-products such as methyl iodide and methyl acetate flowed out through the top of the first distillation column and were recycled to the reactor. A high-boiling fraction containing the catalyst flowed out through the bottom of the column and was recycled to the reactor.

The composition of the iodine compound-containing mixture of methyl acetate, acetic anhydride and acetic acid obtained through the side stream of the distillation column and to be treated by the process of the present invention was as follows:

| | |
|---|---|
| methyl iodide | 8.1 wt. % |
| acetone | 1.2 wt. % |
| methyl acetate | 26.0 wt. % |
| acetic acid | 32.0 wt. % |
| acetic anhydride | 32.0 wt. % |
| iodine ion o | 1800 ppm | o The determination was conducted by adding water to hydrogen iodide and acetyl iodide to liberate iodide ions.

By the treatment of the mixture thus obtained at 180° C. for 30 min in the treatment tank, the iodine concentration in the resulting mixture was reduced to 100 ppm.

The resulting mixture was distilled in a 30-stage Oldershaw distillation column (the second distillation column) having an inner diameter of 40 mm. The mixture was fed into the 13th stage from the top. Methyl iodide and methyl acetate were removed through the top of the column at a reflux ratio of 5, while an acetic anhydride/acetic acid mixture solution was continuously withdrawn through the bottom of the column. 3 ppm of iodide ions were contained in the obtained acetic anhydride/acetic acid mixture solution.

Comparative Example 1

The treatment conducted in the treatment tank in Example 1 was omitted, and the iodine compound-containing mixture of methyl acetate, acetic anhydride and acetic acid obtained through the side stream of the distillation column in Example 1 was distilled in the 30-stage Oldershaw distillation column (the second distillation column) having an inner diameter of 40 mm. The mixture was fed into the 13th stage from the top. Methyl iodide and methyl acetate were removed through the top of the column at a reflux ratio of 5, while an acetic anhydride/acetic acid mixture solution was continuously withdrawn through the bottom of the column. 1300 ppm of iodide ions were contained in the obtained acetic anhydride/acetic acid mixture solution.

Example 2

Methanol was added in such an amount that the concentration thereof would be 7% by weight into the iodine compound-containing mixture of methyl acetate, acetic anhydride and acetic acid obtained through the side stream of the distillation column in Example 1, and the treatment of the mixture thus obtained was conducted at 180° C. for 30 min in the treatment tank. After the completion of the treatment, iodide ion concentration in the resulting mixture was as low as 5 ppm. The determination of the iodide ion concentration was conducted by adding water to hydrogen iodide and acetyl iodide to liberate iodide ions. The resulting mixture was distilled in the 30-stage Oldershaw distillation column (the second distillation column) having an inner diameter of 40 mm. The resulting mixture was fed into the 13th stage from the top. Methyl iodide and methyl acetate were removed through the top of the column at a reflux ratio of 3, while an acetic anhydride/acetic acid mixture solution was continuously withdrawn through the bottom of the column. 1 ppm of iodide ions were contained in the obtained acetic anhydride/acetic acid mixture solution.

Example 3

A 10 wt. % aqueous potassium hydroxide solution was added to the iodine compound-containing mixture of methyl acetate, acetic anhydride and acetic acid containing 5 ppm of iodide ions, which was obtained in Example 2 through heat treatment. The amount of the former solution was 0.3 g per liter of the latter mixture. The resulting mixture was distilled in the 30-stage Oldershaw distillation column (the second distillation column) having an inner diameter of 40 mm in the same manner as that of Example 1.

The iodide ion concentration in the mixture comprising acetic anhydride and acetic acid obtained through the bottom of the column was not higher than 0.01 ppm.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A method for removing iodine compounds contained in crude acetic anhydride formed through the reaction of at least one of dimethyl ether and methyl acetate with carbon monoxide in the presence of an iodide as a reaction promoter, a rhodium compound as a catalyst and methyl iodide as a cocatalyst in a reactor, comprising the steps of: recovering a crude reaction liquid containing acetic anhydride, methyl iodide, methyl acetate and catalyst from the reactor; flash-distilling the crude reaction liquid to separate it into a vapor phase mainly comprising acetic anhydride, methyl iodide, methyl acetate and a liquid phase containing catalyst; returning the liquid phase containing catalyst to the reactor; feeding the vapor phase mainly comprising acetic anhydride, methyl iodide, methyl acetate to a first distillation column; removing a low boiling point fraction containing methyl iodide and methyl acetate as overheads from the top of the first distillation column; returning the overheads to the reactor; returning the bottoms to the reactor; removing crude acetic anhydride as a sidestream from a lower portion of the distillation column; introducing the sidestream of crude acetic anhydride into a treatment tank; heat-treating the sidestream of crude acetic anhydride in the presence of at least one of methanol and methyl acetate at a temperature of from 110° to 200° C. for a time of from 5 to 60 minutes to convert iodine compounds contained therein into methyl iodide, the amount of the at least one of methanol and methyl acetate in the treatment tank being from 1 to 1000 mol in total per mole of iodine compound; feeding the heat-treated crude acetic anhydride to a second distillation column; removing methyl iodide from the top of the column and recovering acetic anhydride from the bottom or a sidestream near the bottom of the second distillation column.

2. The method of claim 1, wherein acetic acid is also produced in the reaction and at least one of water and methanol is present in the reactor during the reaction.

3. The method of claim 1, wherein the distillation of the heat-treated crude acetic anhydride is effected in the presence of at least one of an alkali metal salt and an alkaline earth metal salt.

4. The method of claim 3, wherein the amount of the at least one of an alkali metal salt and an alkaline earth metal salt is from 1 to 10 mol in total per mole of remaining iodine compound.

5. The method of claim 1, wherein the amount of the at least one of methanol and methyl acetate in the treatment tank is from 10 to 500 mol in total per mole of iodine compound.

6. The method of claim 1, wherein hydrogen is present in the reactor during the reaction.

* * * * *